United States Patent [19]

Lafferty et al.

[11] Patent Number: 4,957,861

[45] Date of Patent: * Sep. 18, 1990

[54] PROCESS FOR THE BIOTECHNOLOGICAL PREPARATION OF POLY-D-(−)-3-HYDROXYBUTYRIC ACID

[75] Inventors: Robert M. Lafferty; Gerhart Braunegg, both of Graz, Austria

[73] Assignee: Petrochemie Danubia Ges.m.b.H., Mannsworth, Austria

[*] Notice: The portion of the term of this patent subsequent to Nov. 22, 2005 has been disclaimed.

[21] Appl. No.: 123,085

[22] Filed: Nov. 20, 1987

Related U.S. Application Data

[63] Continuation of Ser. No. 675,970, Nov. 23, 1984, abandoned.

[30] Foreign Application Priority Data

Dec. 1, 1983 [DE] Fed. Rep. of Germany ....... 3343576

[51] Int. Cl.$^5$ ............................ C12P 7/42; C12N 1/20
[52] U.S. Cl. .................................. 435/146; 435/252.1; 435/829
[58] Field of Search ....................... 435/146, 252.1, 829

[56] References Cited

U.S. PATENT DOCUMENTS 4,138,291  2/1979  Lafferty ............................. 435/253
4,786,598  11/1988  Lafferty et al. ..................... 435/146

FOREIGN PATENT DOCUMENTS 015669  9/1980  European Pat. Off. ............ 435/146
046344  2/1982  European Pat. Off. ............ 435/146

OTHER PUBLICATIONS

Lafferty et al., Third European Congress on Biotechnology, Sep. 1984, vol. 1, No. 3, pp. 521–527.
Malik et al; "Nitrogen Fixation by the Hydrogen-Oxidizing Bacterium *Alcaligens latus*"; Arch. Microbial, vol. 129 (1981), pp. 254–256.

Primary Examiner—Elizabeth C. Weimar
Assistant Examiner—Charles L. Patterson, Jr.
Attorney, Agent, or Firm—Mark Dryer

[57] ABSTRACT

The present invention relates to a process for the biotechnological preparation of poly-D-(−)-3-hydroxybutyric acid, herein referred to as PHB, which comprises culturing a microorganism that is a strain of *Alcaligenes latus* or a PHB-producing mutant thereof with unrestricted supply of nutrients, under unlimited growth conditions in the temperature range from 36° to 42° C. at a dissolved oxygen content of 25 to 50% of the saturation value for air and a pH value of 6.0 to 7.5. The PHB is then isolated in the customary manner from the biomass thereby obtained.

14 Claims, No Drawings

PROCESS FOR THE BIOTECHNOLOGICAL PREPARATION OF POLY-D-(−)-3-HYDROXYBUTYRIC ACID

This is a continuation of application Ser. No. 675970, filed on Nov. 23, 1984, now abandoned.

The present invention relates to a process for the biotechnological preparation of poly-D-(−)-3-hydroxybutyric acid hereinafter referred to as (PHB) with a high yield coefficient and an improved enrichment of PHB in the bacterial cell material.

It has been known for a relatively long time that a large number of microorganisms of procaryotic nature are capable of accumulating PHB as a stored substance for energy and carbon inside their cells. The PHB isolated from the cell material of the microorganism is a thermoplastic polyester with advantageous physical properties which suggest that it can be used for purposes similar to those for which, for example, polyethylene or polystyrene are at present available. Compared with these polymers which are customary today, however, PHB has the advantage that it is accessible via a biotechnological route and can also be degraded again by a biological route.

It is also already known that aerobic culturing of PHB-storing microorganisms can be preferentially controlled in the direction of cell division and growth or in the direction of PHB storage inside the cells by the specific composition of the nutrient medium. In the known processes, enrichment of PHB in the cells of the microorganism is achieved if the concentration of the carbon source in the nutrient medium is high in relation to the supply of other nutrients required for growth, for example nitrogen and phosphorus, and the microorganism is cultured, for example, under ammonium-limited growth conditions.

A two-stage process for the preparation of PHB which is based on this knowledge is described, for example, in European Patent A-15,669. In this process, a microorganism of the genus *Methylobacterium organophilium* is first cultured with an unrestricted supply of nutrients, including a complete and adequate supply of nitrogen and phosphorus, until the microorganism population has reached a concentration of, preferably, 20 to 25 g of biomass per liter of culture liquid, without accumulation of PHB inside the cells occurring in this growth phase. Complete interruption of the nitrogen and/or phosphorus supply of the culture medium in the second fermentation stage then causes a stop in reproduction and bacterial growth, accumulation of PHB inside the cells first occurring in this phase. According to the statements of European Patent A-15,669, biomasses with a PHB content of at most 25 to 47% by weight of the cell dry weight are obtained in this process.

A fermentation process for the preparation of PHB which is improved in respect of the above process is described in European Patent A-46,344, this process being based on continuous aerobic culturing of microorganisms of the species *Alcaligenes eutrophus*. According to the statements made in that publication, it is possible in this process to achieve controlled growth of the microorganism population and at the same time enrichment of PHB inside the cells by restricting, in contrast to the process of European Patent A-15,669, the supply of the nutrients and trace substances essential for growth, in particular the supply of nitrogen, from the start of culturing. Although better utilization of the source of carbon in the nutrient medium and an improved accumulation of the PHB is achieved in this manner, the process has the disadvantage that both the specific growth rate and the PHB product formation rate are significantly reduced by the deficient supply of nutrients essential for growth.

Another disadvantage of this process is that with the species *Alcaligenes eutrophus*, the optimum temperature range for fermentation is relatively low. The microorganism must therefore be cultured with severe cooling at 30° to 34° C. in a temperature range in which both growth and accumulation of PHB proceed more slowly than in the case of microorganisms with a higher thermotolerance, which can be cultured at a higher temperature.

For the reasons mentioned, the profitability of the PHB preparation in the known processes is adversely affected by the long residence times in the fermenter, which are necessary for culture of a biomass with a satisfactory accumulated amount of PHB.

Of the carbohydrates, the source of carbon in the process of European Patent A-46,344 is above all fructose, and only in the case where particular mutants derived from the strain *Alcaligenes eutrophus* H 16 are used can a deviation be made to glucose as the nutrient source. Apart from the fact that culture and harvesting of the mutants from the parent strain is labor-intensive, the amount of utilizable nutrient sources, which would enable economical preparation of PHB, which can be obtained by using these mutants is not substantially increased, since the large amounts of disaccharides which are available and serve as a main supply of glucose, for example the sucrose contained in molasses or industrial sugar solutions, also cannot be utilized for the mutants derived from *Alcaligenes eutrophus* H 16.

Although other species of the genus *Alcaligenes*, besides *Alcaligenes eutrophus*, are mentioned in European Patent A-46,344 as being useful for accumulation of PHB, for example *Alc. faecalis, Alc. ruhlandii, Alc. latus* and *Alc. aquamarinus*, further details of the culture and enrichment conditions are not given for any of these species and the procedure of the invention is disclosed in the description and in the examples only for strains of *Alcaligenes eutrophus*.

In contrast, this invention is based on the object of providing a more economical process for the biotechnological preparation of PHB with a high yield coefficient and an improved enrichment of PHB in the cell material of the microorganism utilizing cheaper sources of carbon, in which the disadvantages of the known processes are avoided.

In achieving this object, it has now been found, surprisingly, that a very rapid growth of the microorganism population with simultaneous effective PHB accumulation can be achieved with shorter residence times in the fermenter and the dependency of the microorganism on the nature of the utilizable carbon source can be largely eliminated if strains of the species *Alcaligenes latus* or mutants thereof are cultured in the temperature range from 36° to 42° C. and the fermentation process is carried out under conditions which were not hitherto known in the fermentative preparation of PHB.

Some of the essential features of this new production process for PHB are that, in contrast to the known prior art, the reproduction and rapid growth of the microorganism population is promoted by an optimum, unlimited supply of nutrients, including a complete and adequate supply of nitrogen and phosphorus, and, surprisingly, at the same time an effective intracellular accumulation of PHB is achieved, without the culture being subjected to growth-limiting conditions.

In this manner, biomasses with a significantly better enrichment of PHB than that corresponding to the prior art are formed in the fermenter within shorter residence times, the preparation and isolation of the PHB taking place in a more economical manner than was hitherto possible.

The present invention accordingly relates to a process for the biotechnological preparation of poly-D-(−)-3-hydroxybutyric acid which comprises aerobically culturing a strain of the microorganism *Alcaligenes latus* or a PHB-producing mutant derived from this microorganism in an aqueous nutrient medium containing sources of assimilable carbon, nitrogen and phosphorus and the amount of trace nutrients required for the growth of the microorganism wherein the source of nitrogen is a water-soluble ammonium salt with a complete supply of nutrients optimum for the growth of the microorganism, under unlimited growth conditions in the temperature range from 36° to 42° C. at a dissolved oxygen content of 25 to 50% of the saturation value for air and a pH value of 6.5 to 7.5, under sterile conditions, and isolating the PHB by extraction from the biomass thereby obtained.

All the known straines of *Alcaligenes latus* are suitable for carrying out the process. Preferred bacterial strains in the process of invention are strains of *Alcaligenes latus* selected from the group consisting of *Alcaligenes latus* DSM No. 1122, DSM Nr. 1123 and DSM No. 1124.

The morphological properties of these strains are described in the literature by Palleroni et al. in Int. Journ. of Systematic Bacteriology 28, 416–428, 1978, and recorded in catalogues of culture collections, for example in the Americal Type Culture Collection (ATCC). Culture samples of the microorganisms identified by DSM numbers are freely obtainable to the expert from the Deutsche Sammlung für Mikroorganismen [German Collection of Microorganisms] in Göttingen of the Gesellschaft für biotechnologische Forschung [Biotechnological Research Association], MBH in Stöckheim, Federal Republic of Germany.

The PHB-accumulating mutants of strains of *Alcaligenes latus* which have been obtained from the parent strains by customary processes are also suitable for carrying out the process according to the invention.

Strains of *Alcaligenes latus* have the property, which is advantageous for economical PHB production, that they are capable of utilizing a wide range of carbon sources for growth and for PHB accumulation. Examples which may be mentioned of carbon sources are carbohydrates, such as D-glucose, D-fructose, lactose, maltose, sucrose, starch, molasses, betaine, green syrup, hydrol and cellulose hydrolysates; organic acids and their esters and salts, such as water-soluble salts of gluconic, 2-ketogluconic, formic, acetic, butyric, isobutyric, L-malonic, D-(−)-tartaric, aconitic, itaconic, m-hydroxybenzoic, p-hydroxybenzoic, gentisic, protocatechuic and mandelic acid; alcohols, such as n-propanol, isopropanol, 2,3-butylene glycol, propylene glycol and glycerol; aminoacids, such as β-alanine, L-alanine, L-serine, L-threonine, L-leucine, L-citrulline, L-ornithine, L-aminobutyrate, L-aspartate, L-asparagine, L-glutamate, L-proline, hippurate, sarcosine and creatine; or amines, such as butylamine.

In accordance with their properties as optionally chemolithoautotrophic microorganisms, the strains of Alcaligenes latus are, however, also capable of utilizing carbon dioxide, in addition to the carbon sources so far listed, if the carbon dioxide is available in a mixture together with hydrogen and oxygen as the sole carbon source.

Since the profitability of a biotechnological process for the preparation of PHB very largely depends on the cost of the carbon source in the nutrient substrate, the fact that such a large number of compounds can be used in the fermentation process according to the invention is of great advantage, since the process can be modified for the particular cheapest carbon source.

The excellent utilizability of the readily accessible disaccharides is a surprising and advantageous feature of the process according to the invention, taking into consideration the availability of the nutrient substrate and the profitability of the PHB preparation. In a preferred embodiment, sucrose, which is contained in industrial sugar solutions, for example green syrup, or in waste products of the production of sugar, for example beet molasses, is presented to the microorganism as the source of carbon, culture of the strain *Alcaligenes latus* DSM No. 1123 with sucrose again being particularly advantageous because of the high rate of PHB product formation.

If the assimilatable carbon compounds presented to the microorganism are those from the group which at the same time contain nitrogen in the molecule, the carbon and nitrogen requirement can be met from the same source. Ammonia, ammonium salts, for example ammonium chloride or ammonium sulfate, and nitrates are also utilized by the *Alcaligenes latus* strains as a nitrogen source. The nitrogen requirement necessary can furthermore also be largely met by the nitrogen content of industrial and biological effluents.

The composition of the nutrient solution in respect of its other mineral components includes phosphorus, for example in the form of sodium hydrogen phosphate or potassium hydrogen phosphate, magnesium, for example as magnesium sulfate, calcium, for example as calcium chloride, and iron, for example in the form of iron-III chloride, iron sulfate or iron-III ammonium citrate. Other trace minerals which are essential for growth can preferably be added to the nutrient medium in the form of a trace element solution which has, for example, the following composition:

| | |
|---|---|
| $ZnSO_4.7H_2O$ | 100 mg/l |
| $MnCl_2.4H_2O$ | 30 mg/l |
| $H_3BO_3$ | 300 mg/l |
| $CoCl_2.6H_2O$ | 200 mg/l |
| $CuSO_4.5H_2O$ | 10 mg/l |
| $NiCl_2.6H_2O$ | 20 mg/l |
| $NaMoO_4.2H_2O$ | 30 mg/l |

In carrying out the process according to the invention, a procedure is advantageously followed in which one or more precultures are first prepared, for example in a liquid nutrient medium, and a nutrient solution of the given composition which has been prepared in a production fermenter is inoculated with the well-grown preculture in a ratio of about 1:5 to 1:15.

During the entire duration of culturing, care is taken by supplementing the nutrient substrates consumed, that the sources of carbon, nitrogen and phosphorus and of all the organic and inorganic trace nutrients are kept within the concentration optimum for bacterial growth. Optimum nutrient supply in the context of the present invention is to be understood as meaning culture of the microorganism in a culture medium which, throughout the entire duration of the fermentation, contains all the components of the complete nutrient supply in concentrations such that unlimited growth conditions prevail in the culture and the microorganism experiences no deficiency and no limitation in the supply of nutrients which are essential for growth, for example nitrogen or phosphorus.

The optimum supply of nitrogen for bacterial growth is determined by the method of Warburg, described in Manometric Techniques by Umbreit W. W., Burris R. H., Stauffer J. S., Burges Publishing Company, Minneapolis, U.S.A., 1964, using a Warburg respirator. For strains of *Alcaligenes latus*, the optimum nitrogen supply, without providing limiting conditions for growth, as a rule exists when a concentration of at least 200 mg of ammonium sulfate per liter of culture liquid, corresponding to a nitrogen concentration of at least 45 mg/l, is present in the culture medium throughout the entire fermentation, a nitrogen concentration of about 50 to 700 mg/l being preferred, and a concentration of 80 to 320 mg/l being in turn particularly preferred.

For optimum phosphorus supply, a concentration of at least 500 mg/l of phosphorus is recommended, and it is in turn particularly preferable to maintain a concentration of 600 mg/l to 1.2 g/l. An optimum nutrient solution contains, for example, 10–40 g of sucrose per liter of culture medium as a source of carbon.

Surprisingly, in the culture of strains of *Alcaligenes latus* under the conditions according to the invention, no pronounced accumulation phase for PHB occurs as a function of a nutrient limitation, for example by deficient supply of nitrogen, but an extremely efficient PHB accumulation associated with the growth is to be observed under favorable growth conditions for the microorganism, with complete nutrient supply. This growth-associated PHB enrichment manifests itself, inter alia, in the fact that the percentage content of PHB in the cells is never below 60% by weight of the cell dry weight, for example, in the course of culture.

The growth-associated PHB accumulation with unrestricted nutrient supply has the advantage that neither the specific growth rate nor the PHB product formation rate is reduced by nutrient deficiency, and therefore a higher concentration of biomass with a better PHB enrichment can be obtained within considerably shorter fermentation times than in the case of the known processes which operate with limited nutrient supply.

Whilst maintaining the culture conditions according to the invention, it is possible, for example, to harvest 52.2 g of dry biomass with a PHB content of 74% of the cell dry weight per liter of culture liquid after a residence time in the fermenter of 34 hours.

The culture in the fermenter is advantageously continued under the stated conditions until the biomass formed has reached a PHB content of at least 60% by weight, preferably 70–80% by weight, of the cell dry weight. It is advantageous to establish the continuous supply of the nutrient medium with the nitrogen source such that the lower limiting value of the nitrogen concentration necessary for complete nutrient supply, that is to say a concentration of about 45 mg of nitrogen per liter of culture liquid, is only achieved, or the concentration falls below this value, when the PHB content is at least 60% by weight, but preferably 70–80% by weight, of the cell dry weight.

The pH value of the nutrient solution is advantageously adjusted to values between 6.5 and 7.5, preferably to values from 6.8 to 7.2, by continuous addition of buffer solution, for example of phosphate buffer solution or of aqueous base, for example potassium hydroxide solution or sodium hydroxide solution.

Culture is effected under aerobic conditions, for example with the supply of oxygen or air, the dissolved oxygen content advantageously being maintained in a range from 25 to 50% of the saturation value for air by varying the amount of air or oxygen introduced per unit time. To promote unimpeded growth and PHB enrichment, it is advantageous to introduce sterile air into the stirred culture medium. It is also possible to keep the dissolved oxygen content within the desired range by varying the stirrer speed.

In contrast to the species *Alcaligenes eutrophus*, the strains of *Alcaligenes latus* are surprisingly more thermotolerant. This increased thermotolerance is manifested by the fact that the optimum temperature range for fermentation is 36° to 42° C., a temperature of 37° to 39° C. in turn being particularly preferred. Besides the accelerating effect on growth and PHB accumulation, culture in this temperature range has the advantage that the cooling costs can be considerably reduced during fermentation. The saving in cooling costs by culture at a higher temperature, together with the shorter residence times, is of particular importance, since the cooling costs as a rule make up half of the energy costs which arise during operation of a fermenter.

Under the conditions stated, the culture can be carried out batchwise, for example by a single addition or several additions of nutrient solution. However, it is also possible to operate the fermenter by the feed process route. The feed process comprises feeding in individual, several or all of the components of the nutrient solution to the growing culture of the microorganism in sterile form periodically or continuously during culture, until the operating volume of the fermeter is reached.

Compared with the batchwise process, the feed process has the advantage that the concentration of the nutrients can be kept approximately constant within the desired range, until the useful volume of the fermenter is reached.

However, it is particularly advantageous to carry out the fermentation in a continuous procedure in which a constant stream of fresh nutrient solution is fed to the culture, on the one hand, and, on the other hand, an amount of biomass-containing culture medium equivalent to the feed is removed from the fermenter. As a result of the growth-associated PHB formation which proceeds at at higher rate, high dilution rates (D) of about 0.4 to 0.35 per hour can also be achieved in continuous operation at a PHB enrichment of 70 to 80% by weight of the cell dry weight. The dilution rate (D) is the reciprocal value of the average residence time. In all cases, care is taken that supplementation of the nutrient substrates is effected under sterile conditions.

If carbohydrates are used as the source of carbon, yield coefficients $Y_{x/s}$ of 0.42 to 0.46 are achieved in the process according to the invention, that is to say 0.42 to 0.46 gram of cell dry weight are isolated in the form of PHB-containing biomass per gram of carbohydrate employed. If molasses or green syrup are used as the source of carbon in the nutrient solution, it is possible to achieve yield coefficients of $Y_{x/s}=0.6$ to 0.75, based on the amount of sucrose.

To isolate the PHB, the cell masses are separated off from the nutrient solution by decanting, filtering or centrifuging and the PHB is isolated therefrom by extraction in the customary manner, for example by the process of U.S. Pat. No. 4,101,533.

The nutrient solution which has been freed from the biomass can be recycled to the fermenter, for utilization of the remaining nutrients, and fresh nutrient solution can be added to achieve the optimum nutrient concentration. This nutrient solution can then be used for further cultures.

The following examples illustrate the invention:

EXAMPLE 1

4 liters of an aqueous medium I are introduced in sterilized form into a stirred fermenter. 1 liter of an aqueous solution containing 125 g/l of sucrose is then filtered in, under sterile conditions, and the contents of the fermenter are warmed to 36° C. Medium I has the following composition per liter of deionized water:

| | |
|---|---|
| $Na_2HPO_4.2H_2O$ | 4.5 g/l |
| $KH_2PO_4$ | 1.5 g/l |
| $MgSO_4.7H_2O$ | 0.2 g/l |
| $(NH_4)_2SO_4$ | 0.8 g/l |
| $CaCl_2.2H_2O$ | 0.02 g/l |
| Trace solution | 2 ml/l |
| Fe-III $NH_4$ citrate (17% of Fe): | 0.05 g/l |

The trace solution has the following composition:

| | |
|---|---|
| $ZnSO_4.7H_2O$ | 100 mg/l |
| $MnCl_2.4H_2O$ | 30 mg/l |
| $H_3BO_3$ | 300 mg/l |
| $CoCl_2.6H_2O$ | 200 mg/l |
| $CuSO_4.5H_2O$ | 10 mg/l |
| $NiCl_2.6H_2O$ | 20 mg/l |
| $NaMoO_4.2H_2O$ | 30 mg/l |

The medium is inoculated with a preculture of *Alcaligenes latus* strain DSM 1124 and culture of the microorganism is continued under aerobic conditions at a dissolved oxygen partial pressure of between 25 and 35% of the saturation value for air. During the fermentation, the pH value of the nutrient solution is kept constant at 7.0 by automatic titration with a 10% strength sterile aqueous NaOH solution. In the further course of the fermentation, care is taken, by several additions of sucrose and ammonium sulfate, that the concentration of these substrates never falls below 10% of the starting value. After a residence time of 39 hours in the fermenter, 47.6 g/l of dry biomass with a PHB content of 69% by weight have formed. The yield coefficient $Y_{x/s}$ (g of cell dry weight/g of sucrose employed)=0.45.

EXAMPLE 2

A microorganism of the strain *Alcaligenes latus* DSM 1123 is cultured at a temperature of 38° C. under the process conditions stated in Example 1. After a residence time in the fermenter of 34 hours, 51.3 g/l of dry biomass with a PHB content of 73.8% by weight have formed. The yield coefficient $Y_{x/s}=0.46$.

EXAMPLE 3

A microorganism of the strain *Alcaligenes latus* DSM 1122 is cultured at a temperature of 36° C. under the process conditions stated in Example 1. After a residence time of 37 hours in the fermenter, 48.1 g/l of dry biomass with a PHB content of 70.2% by weight have formed. The yield coefficient $Y_{x/s}=0.45$.

EXAMPLE 4

20 liters of a culture medium containing an initial concentration of 2.2 g/l of $(NH_4)_2SO_4$ and 22 g/l of sucrose as the source of carbon, and otherwise having during fermentation remain unchanged, both in respect of the biomass concentration achieved and the percentage PHB content in the biomass, and also in respect of the yield coefficient.

EXAMPLE 5

20 liters of a culture medium containing an initial concentration of 15 g/l of sucrose, as the sole source of carbon, and with otherwise the same composition as medium I are inoculated as in Example 4, under the conditions stated in that example.

In the further course of the culture, the feed process is carried out continuously in that the concentrations of the nutrient substrates are kept constant by a feed of fresh nutrient solutions adapted to the consumption rates and the dilution. The fresh nutrient solutions consist of sucrose solution with a concentration of 300 g/l, $(NH_4)_2SO_4$ solution with a concentration of 200 g/l and fresh medium I.

After 28 hours, the maximum operating volume of the fermenter of 100 l is exhausted under these continuous feed conditions. At this point in time, the culture broth contains 46 g/l of dry biomass with a PHB content of 74% by weight. The yield coefficient $Y_{x/s}=0.46$.

As in Example 4, 90% of the contents of the fermenter are removed from the fermenter for working up of the biomass and the residual contents of the fermenter serve as the inoculant for renewed culture by the continuous feed process described. In five further operating cycles, the same results as in the first cycle are obtained in respect of biomass, PHB content and yield coefficient.

EXAMPLE 6

20 liters of a culture medium containing an initial concentration of 1.2 g/l of $(NH_4)_2SO_4$, as the source of nitrogen, and 8 g/l of glucose, as the source of carbon, and with otherwise the same composition as the medium I described in Example 1 are initially introduced, in sterile-filtered form, into a sterile, stirred fermenter with a useful volume of 100 l. The fermenter is then inoculated with 2 l of a well-grown preculture of *Alcaligenes latus* DSM 1122. The dissolved oxygen content is established to a concentration range of 38 to 42% of the saturation value for air by varying the stirrer speed and the aeration rate. During the fermentation, a temperature of 39° C. is maintained and the pH value of the nutrient solution is kept at 7.0 by automatic titration with sterile 10% strength aqueous NaOH solution.

In the further course of the culture, the concentrations of $(NH_4)_2SO_4$ and glucose are kept constant by continuously feeding in fresh nutrient medium I and germ-free solutions of $(NH_4)_2SO_4$ and glucose.

After an operating time of 23 hours under the stated conditions, the maximum operating volume of the reactor is reached. At this point in time, the nutrient solution contains 39 g/l of dry biomass with a PHB content of 74% by weight. The yield coefficient $Y_{x/s}=0.42$.

EXAMPLE 7

The culture is carried out by the discontinuous feed process described in Example 4, green syrup with a sucrose content of 59% by weight being used as the source of carbon. After 31 hours, a biomass concentration of 47 g/l with a PHB content of 71% by weight of the cell dry weight is obtained. The yield coefficient $Y_{x/s}=0.62$, based on the amount of sucrose contained in the green syrup.

EXAMPLE 8

The culture is carried out by the continuous feed process described in Example 5, green syrup with a sucrose content of 59% by weight being used as the source of carbon. After 30 hours, a biomass concentration of 49 g/l with a PHB content of 72% of the cell dry weight is obtained in the fermenter. The yield coefficient $Y_{x/s}=0.62$, based on the amount of sucrose contained in the green syrup.

EXAMPLE 9

The culture is carried out by the discontinuous feed process described in Example 4, beet molasses with a sucrose content of 44% by weight being used as the source of carbon. After 33 hours under the stated conditions, the maximum operating volume of the fermenter is reached. At this point in time, the culture broth contains 44 g/l of dry biomass with a PHB content of 74% by weight. The yield coefficient $Y_{x/s}=0.72$, based on the amount of sucrose contained in the beet molasses.

EXAMPLE 10

The culture is carried out by the continuous feed process described in Example 5, beet molasses with a sucrose content of 44% by weight being used as the source of carbon. Under the given continuous feed conditions, 47 g/l of dry biomass with a PHB content of 71% by weight are obtained after 32 hours. The yield coefficient $Y_{x/s}=0.72$, based on the amount of sucrose contained in the beet molasses.

EXAMPLE 11

10 l of a culture medium containing an initial concentration of 1.5 g/l of $(NH_4)_2SO_4$ and 15 g/l of sucrose, as the source of carbon, and with otherwise the same composition as the medium I described in Example 1, are initially introduced into a sterile fermenter with an operating volume of 15 liters, and are inoculated with 1 l of a well-grown preculture of *Alcaligenes latus* strain DSM 1123. The dissolved oxygen content is kept in the region of 30% of the saturation value for air by varying the stirrer speed and aeration rate. During the fermentation, a temperature of 37° C. is maintained and the pH value is brought to 7.0 by automatic titration with a sterile 10% strength aqueous NaOH solution.

In the further course of the fermentation, the nutrient substrates consumed are supplemented by continuously feeding in $(NH_4)_2SO_4$, sucrose and medium I, analogously to Example 5.

When the maximum operating volume of 15 liters is reached, a continuous procedure is established in that a constant stream of fresh nutrient solutions, on the one hand, is fed to the culture and, on the other hand, a biomass-containing amount of nutrient solution equivalent to the feed is removed from the fermenter, the biomass of the solution being isolated by centrifugation. The nutrient solution freshly fed in contains 40 g/l of sucrose, and 4.6 g/l of $(NH_4)_2SO_4$, and corresponds in its remaining composition to medium I.

After some time, a stable equilibrium state is reached, in which the culture broth in the fermenter has a concentration of 16.5 g/l, with a PHB content of 71% by weight of the cell dry weight. The discharge from the fermenter contains a residual concentration of 0.45 g/l of $(NH_4)_2SO_4$ and of 4.1 g/l of sucrose and, after the removal of the biomass and supplementation with fresh nutrient substrates, can be recycled again to the fermenter as nutrient solution.

In the equilibrium state, 6 l/hour of fresh nutrient medium are fed into the fermenter, corresponding to a dilution rate of $D=0.4$ hour$^{-1}$. The yield coefficient $Y_{x/s}=0.46$. The continuous procedure can be maintained for several weeks, without changes resulting in respect of the yield coefficient or the composition of the biomass. In the following Table 1, the operating conditions and the results of the continuous preparation of PHB with *Alcaligenes latus* strain DSM 1123 are summarized.

| | |
|---|---|
| Operating volume | 15 l |
| Stirring | Crosswise blade stirrer |
| Temperature | 37° C. |
| pH value | 7.0 |
| $O_2$ concentration (% of air saturation) | 30% |
| Dilution rate D | 0.4 |
| Carbon source | sucrose |
| Sucrose concentration in the feed | 40 g/l |
| Nitrogen source | $(NH_4)_2SO_4$ |
| Concentration of $(NH_4)_2SO_4$ in the feed | 4.6 g/l |
| Residual concentration of sucrose | 4.1 g/l |
| Residual concentration of $(NH_4)_2SO_4$ | 0.45 g/l |
| Sucrose consumption | 35.9 g/l |
| $(NH_4)_2SO_4$ consumption | 4.15 g/l |
| Biomass concentration | 16.5 g/l |
| PHB content of the biomass | 71% |
| Biomass productivity | 99.1 g/hour |
| PHB productivity | 70.4 g/hour |
| $Y_{x/sucrose}$ | 0.46 |
| $Y_{x(NH_4)_2SO_4}$ | 3.98 |

What we claim is:

1. A process for the biotechnological preparation of poly-D-(—)-3-hydroxybutyric acid, hereinafter referred to as PHB, which comprises aerobically culturing a strain of the microorganism *Alcaligenes latus* or a PHB-producing mutant derived from this microorganism in an aqueous nutrient medium containing sources of assimilable carbon, nitrogen and phosphorus and the amount of trace nutrients required for the growth of the microorganism, wherein the source of nitrogen is a water-soluble ammonium salt, with a complete supply of nutrients optimum for the growth of the microorganism, under unlimited growth conditions in the temperature range from 36° to 42° C. at a dissolved oxygen content of 25 to 50% of the saturation value for air and a pH value of 6.5 to 7.5, under sterile conditions, and isolating the PHB by extraction from the biomass thereby obtained.

2. Process according to claim 1 in which the strain of *Alcaligenes latus* is selected from the group consisting of

*Alcaligenes latus* DSM No. 1122, DSM No. 1123 and DSM No. 1124.

3. Process according to claim 1 in which sucrose is used as the sole source of carbon.

4. Process according to claim 3 in which the strain *Alcaligenes latus* DSM No. 1123 is cultured.

5. Process according to claim 3 in which the microorganism is cultured in a nutrient medium containing 10 to 40 g of sucrose, as the source of carbon, per liter of culture liquid.

6. Process according to claim 1 in which the microorganism is cultured in a nutrient medium containing 45 to 700 mg of nitrogen per liter of culture liquid throughout the entire duration of the fermentation.

7. Process according to claim 6 in which the microorganism is cultured in a nutrient medium containing 80 to 320 mg of nitrogen per liter of culture liquid.

8. Process according to claim 1 in which the microorganism is cultured in a nutrient medium containing 500 mg to 1.2 g of phosphorus per liter of culture liquid.

9. Process according to claim 1 in which the culturing is continued until the biomass formed has reached a PHB concentration of 70 to 80% by weight of the cell dry weight.

10. Process according to claim 1 in which the culturing is carried out at a pH value of 6.8 to 7.2.

11. Process according to claim 1 in which the culturing is carried out at a temperature of 37° to 39° C.

12. Process according to claim 1 in which the culturing is carried out by the feed process route.

13. Process according to claim 1 in which the culturing is carried out continuously.

14. Process according to claim 1 in which after removal of the biomass, the nutrient solution is recycled to the fermentator and supplemented with fresh nutrient solution for further culturing.

* * * * *